United States Patent
Nakamura et al.

(10) Patent No.: US 9,896,703 B2
(45) Date of Patent: Feb. 20, 2018

(54) METHOD FOR PRODUCING TRANSESTERIFIED FAT AND/OR OIL

(71) Applicant: The Nisshin OilliO Group Ltd., Chuo-ku (JP)

(72) Inventors: Yousuke Nakamura, Yokosuka (JP); Yuto Nakazawa, Chiba (JP); Yuko Toyama, Hiratsuka (JP); Yoshie Yamauchi, Nagoya (JP); Hidetaka Uehara, Yokosuka (JP)

(73) Assignee: The Nisshin OilliO Group, Ltd., Chuo-ku, Tokyo (JP)

( * ) Notice: Subject to any disclaimer, the term of this patent is extended or adjusted under 35 U.S.C. 154(b) by 0 days.

(21) Appl. No.: 14/390,866

(22) PCT Filed: Mar. 7, 2013

(86) PCT No.: PCT/JP2013/056235
§ 371 (c)(1),
(2) Date: Oct. 6, 2014

(87) PCT Pub. No.: WO2013/150856
PCT Pub. Date: Oct. 10, 2013

(65) Prior Publication Data
US 2015/0299747 A1    Oct. 22, 2015

(30) Foreign Application Priority Data
Apr. 4, 2012  (JP) .................. 2012-085605

(51) Int. Cl.
| C11B 3/10 | (2006.01) |
| C12P 7/64 | (2006.01) |
| C11C 3/10 | (2006.01) |
| C11B 3/00 | (2006.01) |

(52) U.S. Cl.
CPC ............ *C12P 7/6436* (2013.01); *C11B 3/003* (2013.01); *C11B 3/10* (2013.01); *C11C 3/10* (2013.01); *C12P 7/6454* (2013.01)

(58) Field of Classification Search
CPC ........................................ C11C 1/00
See application file for complete search history.

(56) References Cited

U.S. PATENT DOCUMENTS

| 2005/0084941 A1* | 4/2005 | Abe ............... C10L 1/02 435/135 |
| 2008/0057552 A1* | 3/2008 | Lee ............... C11B 3/003 435/134 |
| 2013/0149414 A1 | 6/2013 | Favre et al. |

FOREIGN PATENT DOCUMENTS

| JP | 2-203790 A | | 8/1990 | |
| JP | 06-001996 a | * | 1/1994 | ............... C11C 3/10 |
| JP | 6-1996 A | | 1/1994 | |
| JP | 8-275 A | | 1/1996 | |
| JP | 8-140689 A | | 6/1996 | |
| JP | 2005-304361 A | | 11/2005 | |
| JP | 2009-45033 A | | 3/2009 | |
| JP | 2009045033 A | * | 3/2009 | |
| JP | 2013-49803 A | | 3/2013 | |
| WO | WO 2008/027527 A2 | | 3/2008 | |
| WO | WO 2012-001015 A1 | | 1/2012 | |

OTHER PUBLICATIONS

Richardson "Use of Bleaching, Clays, in Processing Edible Oils" Journal of the American Oil Chemists Society, vol. 55, 1978, 777-780.*
G.J. Sassano et al.: "Gas Chromatography of Triacylglycerols in Palm Oil Fractions with Medium-Polarity Wide-Bore Columns", JAOCS (Journal of the American Oil Chemists' Society), vol. 70, No. 11, pp. 1111-1114, Nov. 1993 (4 pages).
S. Negishi et al.: "Analysis of Regiospecific Distribution of FA of TAG Using the Lipase-Catalyzed Ester-Exchange", JAOCS (Journal of the American Oil Chemists' Society), vol. 80, No. 4, pp. 353-356, 2003 (4 pages).
International Search Report (PCT/ISA/210) dated May 28, 2013, by the Japanese Patent Office as the International Searching Authority for International Application No. PCT/JP2013/056235.
Written Opinion (PCT/ISA/237) dated May 28, 2013, by the Japanese Patent Office as the International Searching Authority for International Application No. PCT/JP2013/056235.
Extended Search Report issued by the European Patent Office in corresponding European Patent Application No. 13771886.2 dated Aug. 25, 2015 (5 pages).
Office Action issued by the Japanese Patent Office in corresponding Japanese Patent Application No. 2012-085605 dated Jul. 4, 2016 (3 pages).

* cited by examiner

*Primary Examiner* — Robert J Yamasaki
*Assistant Examiner* — Charles Zoltan Constantine
(74) *Attorney, Agent, or Firm* — Buchanan, Ingersoll & Rooney PC

(57) ABSTRACT

An object of the present invention is to provide a method in which a fat and/or oil is produced by a transesterification reaction using a lipase. Specifically, the present invention relates to a method for producing a transesterified fat and/or oil, comprising: (1) a low-temperature clay treatment step of bringing a fat and/or oil and a clay into contact with each other at 30 to 80° C. to obtain a reaction substrate; and (2) a step of subjecting the reaction substrate to a transesterification reaction in the presence of a lipase-containing composition.

7 Claims, No Drawings

METHOD FOR PRODUCING TRANSESTERIFIED FAT AND/OR OIL

TECHNICAL FIELD

The present invention relates to the use of a clay (white clay) for a low-temperature clay treatment on a fat and/or oil, by which decrease in activity of an enzyme is suppressed in a subsequent transesterification reaction, so that the enzyme can be stabilized. Specifically, the present invention relates to a method for producing a transesterified fat and/or oil, the method comprising: a low-temperature clay treatment step of bringing a fat and/or oil and a clay into contact with each other at 30 to 80° C. to obtain a reaction substrate; and a step of subjecting the reaction substrate to a transesterification reaction in the presence of a lipase-containing composition.

BACKGROUND ART

Lipases have been widely used for ester synthesis reactions between various carboxylic acids such as fatty acids and alcohols such as monoalcohols and polyols, transesterification reactions between alcohols and carboxylic acid esters, between carboxylic acids and carboxylic acid esters, and between multiple carboxylic acid esters, and the like. Of these reactions, the transesterification reactions are an important technology as methods for producing esters of various fatty acids, sugar esters, and steroid esters, including those for modification of animal or vegetable fats and/or oils. When a lipase, which is a fat and/or oil hydrolyzing enzyme, is used as a catalyst for such a reaction, the transesterification reaction can be carried out under a mild condition of about room temperature to approximately 130° C. In this case, the side reactions are more suppressed and the energy costs are more reduced than in a conventional chemical reaction. Moreover, the lipase used as the catalyst is highly safe, because the lipase is a natural product. Furthermore, because of the substrate specificity and the positional specificity, the target product can be produced efficiently.

Since such a lipase is expensive, attempts have been made to stabilize the enzymatic activity of a lipase by activating the enzymatic activity of the lipase and suppressing decrease in activity of the lipase. For example, before a transesterification of a raw material fat and/or oil is conducted by using a lipase, the raw material fat and/or oil is treated with a substance having amino groups such as an anion exchange resin. In this manner, the decrease in enzymatic activity has been suppressed (Patent Literature 1). In addition, in Patent Literature 1, the raw material fat and/or oil and a clay are brought into contact with each other at 110° C. in a decolorization step. However, this step is intended only for decolorization of the fat and/or oil, and not for suppression of decrease in enzymatic activity. In addition, when the fat and/or oil and the clay are brought into contact with each other at 110° C., the enzyme cannot be activated. As described above, no study has been made to stabilize the enzymatic activity by bringing a raw material fat and/or oil and a clay into contact with each other before a transesterification reaction.

CITATION LIST

Patent Literature

Patent Literature 1:
Patent Literature 1: Japanese Patent Application Publication No. Hei 8-140689

SUMMARY OF INVENTION

An object of the present invention is to provide a method for producing a transesterified fat and/or oil, in which a fat and/or oil is produced by a transesterification reaction using a lipase, and in which a lipase-containing composition can be used repeatedly by suppressing the decrease in activity of the lipase as much as possible.

To achieve the above described object, the present inventors have found that, when a method in which a fat and/or oil is produced by a transesterification reaction using a lipase includes a treatment on a fat and/or oil with a clay under conditions different from those for a decolorization step, a desired transesterified fat and/or oil can be produced in the subsequent transesterification reaction of the fat and/or oil without greatly lowering the activity of the lipase used for the transesterification reaction. This finding has led to the present invention.

Specifically, possible modes of the present invention relate to:

1. A method for producing a transesterified fat and/or oil, comprising:
    (1) a low-temperature clay treatment step of bringing a fat and/or oil and a clay into contact with each other at 30 to 80° C. to obtain a reaction substrate; and
    (2) a step of subjecting the reaction substrate to a transesterification reaction in the presence of a lipase-containing composition.

2. The method according to the above-described 1, wherein
    the fat and/or oil used in the low-temperature clay treatment step is a fat and/or oil subjected to a decolorization treatment step of performing decolorization by contact with a clay at 90 to 150° C.

3. The method according to the above-described 1 or 2, wherein
    in the low-temperature clay treatment step, the reaction substrate is separated from the clay after the contact with the clay.

4. The method according to any one of the above-described 1 to 3, wherein
    the fat and/or oil subjected to the decolorization treatment step is subjected to a deodorization step after the decolorization treatment step.

5. The method according to any one of the above-described 1 to 4, wherein
    the lipase-containing composition is in the form of a powder.

6. The method according to any one of the above-described 1 to 5, wherein
    the low-temperature clay treatment step is further conducted in the presence of a fatty acid ester.

According to the present invention, a fat and/or oil is treated with a clay under a condition different form that in a decolorization step in a method for producing a fat and/or oil by a transesterification reaction, so that the activity of the lipase does not decrease greatly, even when the lipase-containing composition is used repeatedly.

Especially, the activity of the lipase cannot be stabilized by a decolorization step alone in which a fat and/or oil and a clay are brought into contact with each other at a high temperature of 90 to 150° C. In contrast, the present invention makes it possible to dramatically improve the activation and stabilization of the activity of the lipase by the addition of the low-temperature clay treatment step in which a fat and/or oil and a clay are brought into contact with each other at a relatively low-temperature of 30 to 80° C. under a condition different from that in the decolorization step.

DESCRIPTION OF EMBODIMENTS

Method for Producing Transesterified Fat and/or Oil

The present invention provides a method for producing a transesterified fat and/or oil, comprising:

(1) a low-temperature clay treatment step of bringing a fat and/or oil and a clay into contact with each other at 30 to 80° C. to obtain a reaction substrate; and (2) a step of subjecting the reaction substrate to a transesterification reaction in the presence of a lipase-containing composition. This method will be described in detail below.

<Fat and/or Oil>

The fat and/or oil used in the present invention is a fat and/or oil serving as a substrate in the subsequent transesterification reaction. Water, fatty acid esters and fatty acids described later, and the like may be optionally present in the fat and/or oil, in addition to triglycerides.

For example, the fat and/or oil is preferably triglyceride whose constituent fatty acids have 8 to 24 carbon atoms. The fat and/or oil is particularly preferably a vegetable oil, an oil fraction thereof, or a hydrogenated oil thereof. Here, the vegetable oil is, for example, selected from the group consisting of rapeseed oil, soybean oil, sunflower oil, safflower oil, corn oil, olive oil, sesame oil, palm oil, palm kernel oil, cottonseed oil, coconut oil, sal fat and oil, shea butter, illipe butter, kokum butter, cocoa butter, and medium-chain fatty acid triglycerides.

In addition, the fat and/or oil may be a fat and oil-containing composition containing water. It is appropriate that the amount of water contained in the fat and/or oil be, for example, 10 to 5000 ppm, preferably 150 to 5000 ppm, more preferably 150 to 800 ppm, and most preferably 200 to 400 ppm, relative to the total mass of the fat and/or oil.

As the fat and/or oil used in the present invention, a fat and/or oil subjected to any of ordinary fat and/or oil refinement steps and processing steps can be used. The refinement steps include a degumming step, an alkali deacidification step, a water-washing step, a dehydration and drying step, a decolorization step, a deodorization step, a wintering step, and the like. The processing steps include a transesterification reaction step, a hydrogenation step, a blending step, a fractionating step, and the like. A fat and/or oil subjected to one or more of these steps can be used. Especially, it is more preferable to use a fat and/or oil subjected to a decolorization treatment step. In the decolorization treatment step, the fat and/or oil is brought into contact with an adsorbent selected from clays, activated carbon, and the like. In general, the decolorization treatment step is conducted by contact with a clay in the absence of a lipase. As the clay, activated clay, neutral clay, acid clay, or alkali clay can be used. Activated clay or acid clay is particularly preferable. Specifically, the decolorization is conducted by, for example, placing the fat and/or oil and the clay (in an amount of 0.5 to 2% by mass relative to the fat and/or oil) into a decolorization treatment vessel, and bringing the fat and/or oil and the clay into contact with each other under reduced pressure at 90 to 150° C. (preferably 105 to 120° C.) for about 5 to 40 minutes. In this ranges, the decolorization of the fat and/or oil with the clay can be conducted sufficiently. In addition, it is preferable to conduct this decolorization under reduced pressure in order to remove water contained in the clay and enhance the adsorption performance of the clay. As the decolorization treatment vessel, for example, a tank, a column, a filtering apparatus, or the like can be used. When a tank is used, the tank is preferably equipped with an agitator. It is preferable that the clay can be separated from the fat and/or oil by filtration, centrifugation, or the like, after the fat and/or oil and the clay are brought into contact with each other. To facilitate the filtration, the decolorization treatment step may be conducted in the presence of an auxiliary agent such as a filter aid. Examples of the filter aid include inorganic filter aids such as Celite, and organic filter aids such as fibers of cellulose and the like and ground products thereof. Alternatively, the clay may be packed and held in a column or a filtering apparatus, and the fat and/or oil may be passed through the column or the filtering apparatus. The passing of the fat and/or oil is preferable, because the clay can be separated simultaneously with the passing, and the system can be more compact than a tank. As the filtering apparatus, for example, a single-plate filtering apparatus, a filter press, an Amafilter, or the like is preferably used. A tank, column, or filtering apparatus made of glass, plastic, or a metal such as iron or stainless steel can be used. The tank, column, or filtering apparatus is preferably made of a metal from the viewpoint of durability. This decolorization treatment step is intended for decolorization of the fat and/or oil.

The above-described fat and/or oil subjected to the decolorization treatment step may be subjected to other ordinary fat and/or oil refinement steps such as a degumming step, an alkali deacidification step, a water-washing step, a dehydration and drying step, a deodorization step, and a wintering step, before or after the decolorization treatment step. In addition to the refinement steps such as a deodorization step and an wintering step, it is also possible to conduct a processing step such as a transesterification reaction step, a hydrogenation step, a blending step, or a fractionating step. For example, as the fat and/or oil subjected to the decolorization treatment step of the present invention, a fat and/or oil subjected to the decolorization treatment step, transesterification, and further fractionation may be used. Note that the refinement conditions and processing conditions in these steps are those employed in general methods for fats and/or oils.

<Low-Temperature Clay Treatment Step on Fat and/or Oil>

The present invention includes a low-temperature clay treatment step. In the low-temperature clay treatment step, a reaction substrate is obtained by bringing a fat and/or oil, which is to serve as the reaction substrate, and a clay into contact with each other at 30 to 80° C. This treatment step is not a reaction step using a lipase. Hence, a lipase is not essential, and is preferably absent in this treatment step.

Note that, in the reaction substrate, fatty acid esters and fatty acids are also used in some cases, in addition to the fat and/or oil. These fatty acid esters and fatty acids do not necessarily have to be subjected to the low-temperature clay treatment step. However, it is preferable to conduct the low-temperature clay treatment step on a blend of these fatty acid esters and fatty acids with the fat and/or oil, or to conduct the low-temperature clay treatment step on the these fatty acid esters and fatty acids, separately from the low-temperature clay treatment step on the fat and/or oil.

The fatty acid esters are preferably, for example, linear or branched and saturated or unsaturated fatty acid esters having 4 to 30 and preferably 8 to 22 carbon atoms. Here, examples of the fatty acids include octanoic acid, decanoic acid, lauric acid, myristic acid, palmitic acid, stearic acid, oleic acid, linoleic acid, linolenic acid, behenic acid, and the like. Alcohols of the esters are preferably linear or branched saturated alcohols. Here, the alcohols include methanol, ethanol, propanol, higher alcohols, and the like. Particularly preferred fatty acid esters include ethyl palmitate, methyl palmitate, ethyl stearate, methyl stearate, ethyl behenate, methyl behenate, ethyl oleate, and methyl oleate.

The fatty acids are preferably, for example, linear or branched and saturated or unsaturated fatty acids having 4 to 30 preferably 8 to 22 carbon atoms. Here, examples of the fatty acids include octanoic acid, decanoic acid, lauric acid, myristic acid, palmitic acid, stearic acid, oleic acid, linoleic acid, linolenic acid, behenic acid, and the like.

Specifically, the low-temperature clay treatment step is conducted by bringing the fat and/or oil and the clay into contact with each other at 30 to 80° C., for example. As a container for the contact, for example, a tank, a column, a filtering apparatus, or the like can be used as in the case of the above-described decolorization treatment. When a tank is used, the tank is preferably equipped with an agitator. It is preferable that the clay can be separated from the fat and/or oil by filtration, centrifugation, or the like, after the fat and/or oil and the clay are brought into contact with each other. Alternatively, the clay may be packed and held in a column or a filtering apparatus, and the fat and/or oil may be passed through the column or the filtering apparatus. This passing of the fat and/or oil is preferable, because the clay can be separated simultaneously with the passing, and the system can be more compact than a tank. As the filtering apparatus, for example, a single-plate filtering apparatus, a filter press, an Amafilter, or the like is preferably used. A tank, column, or filtering apparatus made of glass, plastic, or a metal such as iron or stainless steel can be used. The tank, column, or filtering apparatus is preferably made of a metal from the viewpoint of durability. This low-temperature clay treatment step is intended for a pretreatment on the fat and/or oil conducted before the transesterification reaction.

The fat and/or oil and the clay are brought into contact with each other at 30 to 80° C., and preferably 50 to 80° C. Within this range, the fat and/or oil can be treated with the clay sufficiently.

It is appropriate that the contact with oxygen be avoided as much as possible, when the fat and/or oil and the clay are brought into contact with each other. When the contact is conducted in a tank, for example, the contact is desirably conducted under reduced pressure or in the presence of an inert gas. The passing thorough a column or a filtering apparatus is preferable, because the column or the filtering apparatus is filled with the fat and/or oil, so that the contact with oxygen hardly occurs. It is particularly preferable to apply a pressure to the low-temperature clay treatment vessel with an inert gas such as nitrogen or argon. In the pressure application, it is appropriate that the pressure be, for example, 0.001 to 10 MPa, and preferably 0.05 to 1 MPa. The reduced pressure can be achieved by using a vacuum pump or the like.

The fat and/or oil and the clay are brought into contact with each other for preferably 5 seconds or more, and more preferably 30 seconds to 30 minutes. The time is further preferably 1 to 15 minutes, and most preferably 2 to 10 minutes. In a case where a tank is used or the like, no adverse effect occurs even when the fat and/or oil and the clay are in contact with each other for a long period, but it is preferable that the contact be conducted for 48 hours or less, in terms of operation. For example, when the contact is conducted by using a column, the fat and/or oil is passed at a mass ratio of 1 to 2000 times, and preferably 200 to 1000 times, relative to 1 kg of the clay. In addition, the flow rate is preferably such that 0.5 to 100 kg of the fat and/or oil is passed through, relative to 1 kg of the clay in 1 hour. Particularly preferably, it is appropriate that 5 to 30 kg of the fat and/or oil be passed in 1 hour. Moreover, the flow rate of the fat and/or oil (or a mixture in a case of a mixture with other substances such as stearic acid ester) is 0.01 to 10 ml/minute, preferably 0.05 to 1 ml/minute, and more preferably 0.1 to 1 ml/minute, per gram of the clay.

By the contact of the fat and/or oil with the clay in this manner, the reaction substrate used in the subsequent transesterification reaction step can be obtained.

The clay used in the low-temperature clay treatment step is, for example, selected from the group consisting of activated clay, neutral clay, acid clay, alkali clay, and mixtures thereof. The clay may be the same as or different from that used in the above-described decolorization treatment step.

Moreover, the above-described low-temperature clay treatment step may be conducted in the presence of an auxiliary agent such as a filter aid. Examples of the filter aid include inorganic filter aids such as Celite and organic filter aids such as fibers of cellulose and the like and ground products thereof. The filter aid is preferably an organic filter aid, especially an organic polymer filter aid, and particularly preferably cellulose powder or the like. The filter aid is preferably in the form of a power. However, it is the most preferable that no filter aid be used, if any problem such as a problem with the pressure during feed of the liquid or leakage during filtration does not occur even without any filter aid. In the low-temperature clay treatment step, the mass ratio of the clay to the filter aid is, for example, 1:10 to 10:1, preferably 1:5 to 5:1, more preferably 1:1 to 3:1, and particularly preferably 2:1.

<Reaction Substrate>

In the present invention, the low-temperature clay treatment step is conducted, and then the transesterification reaction step is conducted. As the reaction substrate, the fat and/or oil subjected to the low-temperature clay treatment step is used. Here, as the reaction substrate, a fat and/or oil subjected to the low-temperature clay treatment step by itself may be used, or a mixture of such fats and/or oils may be used. Moreover, it is also possible to use a mixture of the fat and/or oil subjected to the low-temperature clay treatment step with another reaction substrate such as a fatty acid ester, a fatty acid, or the like. The mixing may be conducted before or after the low-temperature clay treatment step. The fatty acid ester and the fatty acid are preferably distilled. In addition, the fatty acid ester and the fatty acid are preferably subjected to the low-temperature clay treatment step.

Note that it is appropriate that the mass ratio of the fatty acid ester or the fatty acid to the fat and/or oil in the reaction substrate be, for example, 9:1 to 1:9, preferably 8:2 to 2:8, and more preferably 7:3 to 5:5.

<Transesterification Reaction Step>

In the present invention, (2) a step of subjecting the reaction substrate to a transesterification reaction in the presence of a lipase-containing composition is further included.

Conditions of the transesterification reaction of the present invention are not particularly limited, and the transesterification reaction can be carried out in a usual manner.

In general, the transesterification reaction is carried out at normal pressure or reduced pressure, while avoiding contamination with water, which would otherwise cause hydrolysis. The reaction temperature depends on the freezing point of the reaction substrate used and the optimum temperature and stability of the enzyme used. The reaction is preferably carried out at about 20 to 130° C., and if the temperature is not limited by the freezing point, the reaction is more preferably carried out at 40 to 60° C.

Specifically, the transesterification reaction is carried out by, for example, introducing the reaction substrate into a reaction vessel, and bringing the reaction substrate into contact with a lipase in a lipase-containing composition. As the reaction vessel, for example, a tank, a column, a filtering apparatus, or the like can be used. When a tank is used, the tank is preferably equipped with an agitator. It is preferable that the lipase can be removed by filtration or centrifugation, after the raw material and the lipase are brought into contact with each other. Alternatively, a immobilized lipase or a lipase powder may be packed and held in a column or a filtering apparatus, and the reaction substrate is passed through the column or the filtering apparatus to conduct the reaction. As the filtering apparatus here, for example, a single-plate filtering apparatus, a filter press, an Amafilter, or the like is preferably used. A tank, column, or filtering apparatus made of glass, plastic, or a metal such as iron or stainless steel can be used. The tank, column, or filtering apparatus is preferably made of a metal from the viewpoint of durability.

The amount of the lipase-containing composition added varies depending on the type of the lipase and the degree of the activity of the lipase. When an ordinary lipase-containing composition such as a lipase powder or an immobilized lipase is used in a transesterification reaction conducted by a batch process using a tank, it is appropriate that the reaction substrate and the lipase-containing composition be brought into contact with each other, with the amount of the lipase-containing composition added being, for example, 0.05 to 10% by mass, and preferably 0.1 to 5% by mass relative to the total mass of the reaction substrate. Note that, in a batch process, a smaller amount of the lipase is more preferable in terms of costs. The amount of the lipase is adjusted, as appropriate, on the basis of the conditions (activity, optimum temperature, stability, and the like) of the lipase. The contact in this manner is appropriate, because the transesterification reaction can be completed in a reaction time of 1 to 100 hours. Meanwhile, when the transesterification reaction is conducted continuously by using a column or the like, it is appropriate that the reaction substrate be passed at a mass ratio of 100 to 100000 times relative to 1 kg of the lipase-containing composition. Note that the flow rate is preferably such that 0.5 to 200 kg of the reaction substrate be passed through relative to 1 kg of the lipase-containing composition in 1 hour. The flow rate is particularly preferably such that 5 to 100 kg of the reaction substrate is passed therethrough in 1 hour. Note that when a column is used, a larger amount of the reaction substrate passed is more preferable, and a faster flow rate is more preferable from the viewpoint of productivity, as long as the quality of the target reaction oil can be retained. The flow amount and the flow rate thorough the column are adjusted, as appropriate, on the basis of the conditions (activity, optimum temperature, stability, and the like) of the lipase used. The temperature inside the column during the passing is preferably 20 to 90° C., more preferably 30 to 70° C., and most preferably 40 to 60° C. The optimum amount of the lipase-containing composition added and the optimum flow amount of the reaction substrate are determined by the reaction temperature, the setting reaction time, the activity of the lipase in the lipase-containing composition, and the like. By bringing the lipase and the reaction substrate into contact with each other as described above, the fat and/or oil in the reaction substrate can be modified by the transesterification reaction. Thus, a transesterified fat and/or oil can be produced.

The lipase-containing composition of the present invention may be made of lipase alone, or may optionally contain components used in a culture medium of the lipase, an auxiliary agent, and an immobilization support, in addition to the lipase.

Lipases usable in the present invention include lipoprotein lipase, monoacylglycerol lipase, diacylglycerol lipase, triacylglycerol lipase, galactolipase, phospholipase, and the like. Of these lipases, triacylglycerol lipase is preferable.

Microorganisms which produce these lipases include, but are not particularly limited to, bacteria, yeasts, filamentous fungi, actinomycetes, and the like, and specifically include *Alcaligenes* sp., *Pseudomonas* sp., *Arthrobacter* sp., *Staphylococcus* sp., *Torulopsis* sp., *Escherichia* sp., *Mycotorula* sp., *Propionibacterium* sp., *Chromobacterium* sp., *Xanthomonas* sp., *Lactobacillus* sp., *Clostridium* sp., *Candida* sp., *Geotrichum* sp., *Saccharomycopsis* sp., *Nocardia* sp., *Fusarium* sp., *Aspergillus* sp., *Rhizomucor* sp., *Mucor* sp., *Thermomyces* sp., *Rhizopus* sp., *Penicillium* sp., *Phycomyces* sp., *Puccinia* sp., *Bacillus* sp., *Streptomyces* sp., and the like.

In the present invention, a lipase is preferably derived from *Alcaligenes* sp., *Pseudomonas* sp., *Rhizomucor* sp., *Mucor* sp., *Thermomyces* sp., *Rhizopus* sp., or *Penicillium* sp., among the above-described microorganisms. Especially, a lipase from *Alcaligenes* sp. of *Alcaligenes* sp., a lipase from *Rhizomucor miehei* of *Rhizomucor* sp., a lipase from *Thermomyces lanuginosus* of *Thermomyces* sp., a lipase from *Rhizopus delemar* of *Rhizopus* sp., or a lipase from *Rhizopus oryzae* of *Rhizopus* sp. is more preferable. A lipase from *Rhizopus oryzae* is particularly preferable.

The lipase used in the lipase-containing composition of the present invention may be obtained by drying a lipase-containing aqueous liquid containing components of a culture medium in which a lipase is produced, and the like. However, the lipase used is preferably free from these components, i.e., substantially composed of a lipase itself. The lipase-containing composition of the present invention is more preferably one obtained by removing cells after culturing for a lipase and then immobilizing the lipase, or one obtained by further powdering the immobilized lipase.

The lipase used in the present invention may have positional specificity, but does not necessarily have to have positional specificity. When the lipase has positional specificity, the lipase is preferably 1,3-specific.

Form of Lipase-Containing Composition

The lipase-containing composition of the present invention may be in the form of an immobilized material (immobilized lipase) or a powder (lipase powder).

The immobilized lipase is preferably one obtained by immobilizing the above-described lipase onto an immobilization support such as silica, Celite, diatomaceous earth, perlite, polyvinyl alcohol, anion exchange resin, phenol adsorption resin, hydrophobic support, cation exchange resin, or chelating resin. Such an immobilized lipase is available, for example, as Lipozyme TL-IM from Novozymes A/S. The immobilized lipase can be used as it is, or one obtained by grinding the immobilized lipase can be used.

The lipase powder may be used in the form of a lipase powder preparation. The lipase powder preparation is obtained by, for example, drying and powdering a lipase-containing aqueous liquid obtained by dissolving and/or dispersing a lipase and a grain powder and/or a sugar powder in an aqueous liquid.

Among the lipases listed above, Picantase R8000, a product of DSM Japan KK, Lipase F-AP15, a product of Amano Enzyme Inc., or the like is preferably used as the lipase. The most suitable lipase powders include Lipase DF "Amano" 15-K (also referred to as Lipase D) and Lipase D "Amano" Conc, which are products of Amano Enzyme Inc. and derived from *Rhizopus oryzae*.

Examples of the grain powder and/or the sugar powder include soybean powders such as full-fat soybean powder and defatted soybean powder, wheat flour, rice powder, and dextrin. It is appropriate that the amount of the grain powder and/or sugar powder be, for example, 250 to 1000% by mass, preferably, 500 to 1000% by mass, and more preferably 500 to 750% by mass, relative to the lipase.

In addition, a filter aid such as cellulose powder or Celite may be present in the lipase-containing composition. The mass ratio of the lipase to the filter aid is, for example, 1:10 to 10:1, preferably 1:5 to 5:1, more preferably 1:2 to 2:1, and particularly preferably 1:1.

<Separation Step>

Each of the low-temperature clay treatment step (1), the transesterification reaction step (2), and the other optional steps described above may further comprise a step of separating the clay, the lipase-containing composition, or the like from the fat and/or oil, the reaction substrate, or the like. In the separation step, for example, filtration, centrifugation, or the like is employed. A column accommodating the clay is preferable. Here, it is preferable to attach a filter to the column, left only the clay in the column, and filter and separate the fat and/or oil or the reaction substrate from the clay.

The above-described filter is preferably a filter cloth, a filter paper, or a glass filter (pore size: 1 to 10 μm, preferably 5 μm).

EXAMPLES

Next, the present invention will be described in detail based on Production Examples and Examples.

[Preparation of Lipase-Containing Composition A]

An enzyme solution (150000 U/ml) of Lipase DF "Amano" 15-K (also referred to as Lipase D and derived from *Rhizopus oryzae*), which was a product of Amano Enzyme Inc., was prepared. The mass of water in this enzyme solution was 15 times the mass of Lipase D. In addition, as a grain powder, an aqueous solution containing 10% by mass of a deodorized full-fat soybean powder (product name: Alphaplus HS-600, manufactured by The Nisshin OilliO Group, Ltd.) was prepared. The mass of the above-described deodorized full-fat soybean powder was 500% by mass relative to the mass of Lipase D mentioned above. The above-described deodorized full-fat soybean powder was added to the enzyme solution of Lipase D, while the solution was being stirred. The pH of the mixture solution as a whole was adjusted to 7.8 by adding 1 ml of a 0.5 N NaOH solution to the obtained mixture solution. Then, the mixture solution was subjected to a parallel-flow nozzle type spray drying (the temperature of the above-described mixture solution: 30° C., the air inlet temperature: 100° C., the air outlet temperature: 50° C., SD-1000 model of TOKYO RIKAKIKAI CO., LTD.). Thus, a lipase powder preparation A (a lipase powder derived from *Rhizopus oryzae*) was obtained. To this lipase powder preparation A, cellulose powder was added as a filter aid to obtain a lipase-containing composition A. The mass ratio of the lipase powder to the filter aid contained in the obtained lipase-containing composition A was 1:1.

[Preparation of Lipase-Containing Composition B]

A lipase-containing composition B was obtained by grinding 5 g of Lipozyme TL-IM (an immobilized lipase derived from *Thermomyces lanuginosus*), which was a product manufactured by Novozymes A/S, using an L-type Mycolloider manufactured by Tokushu Kika Kogyo Co., Ltd. Note that the average particle diameter of the lipase-containing composition B measured by using a particle size distribution measuring apparatus (LA-500) of HORIBA, Ltd. was 66.7 μm.

[Low-Temperature Clay Treatment Vessel (Column) 1]

A low-temperature clay treatment vessel (column) 1 was prepared (see Fig. 2) by mixing 1 g of an activated clay (product name: GALLEON EARTH V2, manufactured by Mizusawa Industrial Chemicals, Ltd.) with 0.5 g of cellulose powder, and packing this mixture into a glass column (manufactured by TOKYO RIKAKIKAI CO., LTD., inner diameter: 8 mm, length: 100 mm). The column also had a filter like a glass filter (pore size: 5 μm).

[Low-Temperature Clay Treatment Vessel (Column) 2]

A low-temperature clay treatment vessel (column) 2 was prepared in the same manner as for the low-temperature clay treatment vessel (column) 1, except that a neutral clay (product name: PREMIUM, manufactured by WANTOTIK SDN. BHD, pH 6.6) was used instead of the activated clay.

[Low-Temperature Clay Treatment Vessel (Column) 3]

A low-temperature clay treatment vessel (column) 3 was prepared in the same manner as for the low-temperature clay treatment vessel (column) 1, except that an alkali clay (product name: NB14000, manufactured by Natural Bleach SDN. BHD, pH 9.5) was used instead of the activated clay.

[Low-Temperature Clay Treatment Vessel (Column) 4]

A low-temperature clay treatment vessel (column) 4 was prepared in the same manner as for the low-temperature clay treatment vessel (column) 1, except that an alkali clay (product name: KRISTAL, manufactured by Taiko Clay Marketing SDN. BHD, pH 8.5) was used instead of the activated clay.

[Low-Temperature Clay Treatment Vessel (Bed) 5]

Five grams of a neutral clay (product name: PREMIUM, manufactured by WANTOTIK SDN. BHD, pH 6.6) and 2.5 g of a cellulose powder were mixed with each other, and 100 g of a high-oleic sunflower oil was added to this mixture, followed by stirring with a stirrer for 1 hour. After that, the obtained mixture was set onto a single-plate filter (KST-90, manufactured by Advantec Toyo Kaisha, Ltd.) on which a filter paper (5C, 110 mm, manufactured by Advantec Toyo Kaisha, Ltd.) was set, and a pressure of 0.1 MPa was applied using nitrogen. Thus, a low-temperature clay treatment vessel (bed) 5 was prepared.

[Preparation of Reaction Vessel A]

To 0.3 g of the lipase-containing composition A prepared as described above, 10 g of a high-oleic sunflower oil was added, followed by stirring with a stirrer for 1 hour. After that, the mixture was set to a glass column (manufactured by TOKYO RIKAKIKAI CO., LTD., inner diameter: 8 mm, length: 100 mm), and was packed by evacuating the column with a vacuum pump on one side of the column. Thus, a reaction vessel (column) A was prepared (see Fig. 2). This column has a filter like a glass filter (pore size: 5 μm).

[Preparation of Reaction Vessel B]

To 0.5 g of the lipase-containing composition B prepared as described above, 10 g of a high-oleic sunflower oil was added, followed by stirring with a stirrer for 1 hour. After that, the mixture was set to a glass column (manufactured by TOKYO RIKAKIKAI CO., LTD., inner diameter: 8 mm, length: 100 mm), and packed by evacuating the column with a vacuum pump on one side of the column. Thus, a reaction vessel (column) B was prepared.

[Evaluation Methods]

Evaluation was made by selecting one of the following methods depending on the reaction substrate and the difference in 1,3-selectivity of the lipase.

Activity (XOX %) in Transesterification Reaction

In each case where the activity of a lipase with a high 1,3-selectivity was investigated by using a fat and/or oil and ethyl stearate as the reaction substrate, the degree (stability) of the lipase activity was evaluated by comparing the total mass of POS and SOS among triglycerides. Specifically, a fat and/or oil obtained in a transesterification reaction using a lipase-containing composition was analyzed by gas chromatography. The percentage of the total mass of POS (1-stearoyl-2-oleoyl-3-palmitoyl glycerin or 1-palmitoyl-2-oleoyl-3-stearoyl glycerin) and SOS (1,3-distearoyl-2-oleoyl glycerin), among triglycerides, relative to the mass of all triglycerides was defined as XOX %, and the XOX was compared among Examples and Comparative Examples.

(XOX %)=(percentage of mass of POS among triglycerides)+(percentage of mass of SOS among triglycerides)

A high XOX % value indicates that the lipase activity is high, i.e., the lipase can be used stably.

Activity (SOO %) in Transesterification Reaction

In each case where the activity of a lipase with a low 1,3-selectivity was investigated by using a fat and/or oil and ethyl stearate as the reaction substrate, the degree (stability) of the lipase activity was evaluated by comparing the mass of SOO among the triglycerides. Specifically, a fat and/or oil obtained in a transesterification reaction using a lipase-containing composition was analyzed by gas chromatography. The percentage of the total mass of SOO (1-stearoyl-2,3-dioleoyl glycerin or 1,2-dioleoyl-3-stearoyl glycerin), among triglycerides, relative to the mass of all triglycerides was defined as SOO %, and the SOO was compared among Examples and Comparative Examples. A high SOO % value indicates that the lipase activity is high, i.e., the lipase can be used stably.

Activity (C44%) in Transesterification Reaction

In each case where a fat and/or oil and a medium-chain fatty acid triglyceride were used as the reaction substrate, the degree (stability) of the lipase activity was evaluated by comparing the total mass of triglycerides in each of which the total number of carbon atoms of fatty acids bound was 44. Specifically, a fat and/or oil obtained in a transesterification reaction using a lipase-containing composition was analyzed by gas chromatography, and the percentage of the total mass of capryl-dioleoyl glycerin, capryl-distearoyl glycerin, and the like, among triglycerides, relative to the mass of all triglycerides was defined as C44%, and the C44 was compared among Examples and Comparative Examples. A high C44% value indicates that the lipase activity is high, i.e., the lipase can be used stably.

[Analysis Methods]

The percentage of the mass of POS, the percentage of the mass of SOS, and the percentage of the mass of SOO among triglycerides were determined by the method according to JAOCS (Journal of The American Oil Chemists' Society). vol. 70, no. 11, pp. 1111-1114 (1993). The percentage of the mass of C44 among triglycerides was determined by the method according to JAOCS (Journal of The American Oil Chemists' Society). vol. 80, no. 4, pp. 353-356 (2003).

Comparative Example 1

A crude high-oleic sunflower oil was decolorized at 110° C. for 20 minutes by using 1% by mass of an activated clay (product name: GALLEON EARTH V2, manufactured by Mizusawa Industrial Chemicals, Ltd.), and then deodorized by keeping the oil at 260° C. for 90 minutes under 400 Pa. Thus, a refined high-oleic sunflower oil was obtained. Ethyl stearate (product name: Ethyl Stearate, manufactured by Inoue Perfumery MFG. Co., Ltd.) and the refined high-oleic sunflower oil were mixed with each other at a mass ratio of 6:4. Then, the mass fraction of water in the oil was adjusted to 200 ppm. Thus, a reaction substrate 1 was prepared. The temperatures of a reaction vessel A prepared as described above and the reaction substrate 1 were adjusted to 50° C., and the reaction substrate 1 was fed to the reaction vessel A (column) at a rate of 0.2 ml/minute for 64 hours. Thus, a transesterified fat and oil 1 was obtained. The XOX (%) of the transesterified fat and oil obtained through an outlet of the reaction vessel 64 hours after the start of the reaction was analyzed.

Comparative Example 2

A neutral clay (product name: PREMIUM, manufactured by WANTOTIK SDN. BHD) was added to each of the ethyl stearate and the refined high-oleic sunflower oil used in Comparative Example 1 at a ratio of 2% by mass relative to the ethyl stearate or the refined high-oleic sunflower oil, and each mixture was heated under reduced pressure at 110° C. for 20 minutes. After that, the clay was removed by filtration. Thus, a decolorized ethyl stearate and a re-decolorized high-oleic sunflower oil 1 was obtained. The obtained decolorized ethyl stearate and the re-decolorized high-oleic sunflower oil 1 were blended at a mass ratio of 6:4, and the mass fraction of water in the oil was adjusted to 200 ppm. Thus, a reaction substrate 2 was obtained.

Re-decolorized high-oleic sunflower oils 2 and 3 were each obtained in the same manner as for the above-described re-decolorized high-oleic sunflower oil 1, except that an alkali clay (product name: NB14000, manufactured by Natural Bleach SDN. BHD) or an alkali clay (product name: KRISTAL, manufactured by Taiko Clay Marketing SDN. BHD) was used instead of the above-described neutral clay (product name: PREMIUM, manufactured by WANTOTIK SDN. BHD). Reaction substrates 3 and 4 were each obtained in the same manner as for the above-described reaction substrate 2, except that the re-decolorized high-oleic sunflower oil 2 or 3 was used instead of the above-described re-decolorized high-oleic sunflower oil 1. The temperatures of reaction vessels A (columns) prepared as described above and the reaction substrates 2 to 4 were adjusted to 50° C., and each of the reaction substrates 2 to 4 was fed to one of the reaction vessels A (columns) at a rate of 0.2 ml/minute for 64 hours. Thus, transesterified fats and oils 2 to 4 were obtained. The XOX (%) of each of the transesterified fats and oils 2 to 4 obtained through an outlet of the reaction vessel 64 hours after the start of the reaction was analyzed.

Comparative Example 3

Each of the re-decolorized high-oleic sunflower oils 1 to 3 obtained in Comparative Example 2 was deodorized by heating at 250° C. for 90 minutes under a reduced pressure of 500 Pa, while steam was being blown. Thus, re-decolorized and deodorized high-oleic sunflower oils 1 to 3 were obtained. Each of the obtained re-decolorized and deodorized high-oleic sunflower oils 1 to 3 was mixed with the decolorized ethyl stearate obtained in Comparative Example 2 at a ratio (mass ratio) of 4:6, and then the mass fraction of water in the oil was adjusted to 200 ppm. Thus, reaction substrates 5 to 7 were each obtained. The temperatures of reaction vessels A (columns) prepared as described above and the reaction substrates 5 to 7 were adjusted to 50° C., and each of the reaction substrates 5 to 7 was fed to one of the reaction vessels A (columns) at a rate of 0.2 ml/minute for 64 hours. Thus, transesterified fats and oils 5 to 7 were each obtained. The XOX (%) of each of the transesterification oils 5 to 7 obtained through an outlet of the reaction vessel 64 hours after the start of the reaction was analyzed.

Example 1

The temperatures of low-temperature clay treatment vessels 1 to 4 described above were adjusted to 50° C., and a mixture oil obtained by mixing the refined high-oleic sunflower oil and the ethyl stearate used in Comparative Example 1 at a ratio (mass ratio) of 4:6 was fed to each of the low-temperature clay treatment vessels 1 to 4 (at 50° C.) at a rate of 0.2 ml/minute. Then, the mass fraction of water in each oil was adjusted to 200 ppm. Thus, reaction substrates 8 to 11 were each obtained. Each of the mixture oils was brought into contact with the clay for 10 minutes. The temperatures of reaction vessels A prepared as described above and the reaction substrates 8 to 11 were adjusted to 50° C., and each of the reaction substrates 8 to 11 was fed to one of the reaction vessels A at a rate of 0.2 ml/minute for 64 hours. Thus, transesterified fats and oils 8 to 11 were each obtained. The XOX (%) of each of the transesterified fats and oils 8 to 11 obtained through an outlet of the reaction vessel 64 hours after the start of the reaction was analyzed.

TABLE 1

| | Comp. Ex. 1 | Comp. Ex. 2 | | | Comp. Ex. 3 | | |
|---|---|---|---|---|---|---|---|
| Clay | — | PREMIUM | NB14000 | KRISTAL | PREMIUM | NB14000 | KRISTAL |
| Clay treatment vessel | — | (re-decolorization) | (re-decolorization) | (re-decolorization) | (re-decolorization and deodorization) | (re-decolorization and deodorization) | (re-decolorization and deodorization) |
| Reaction vessel | A | A | A | A | A | A | A |
| Reaction substrate | 1 | 2 | 3 | 4 | 5 | 6 | 7 |
| Transesterified fat and oil | 1 | 2 | 3 | 4 | 5 | 6 | 7 |
| Clay treatment temperature | — | | | | 110° C. | | |
| XOX (%) | 25.2 | 27.2 | 24.3 | 23 | 27.5 | 27.6 | 23.1 |

TABLE 2

| | Example 1 | | | |
|---|---|---|---|---|
| Clay | GALLEON EARTH V2 | PREMIUM | NB14000 | KRISTAL |
| Clay treatment vessel | 1 | 2 | 3 | 4 |
| Reaction vessel | A | A | A | A |
| Reaction substrate | 8 | 9 | 10 | 11 |
| Transesterified fat and oil | 8 | 9 | 10 | 11 |

TABLE 2-continued

| | Example 1 | | | |
|---|---|---|---|---|
| Clay | GALLEON EARTH V2 | PREMIUM | NB14000 | KRISTAL |
| Clay treatment temperature | | 50° C. | | |
| XOX(%) | 33.0 | 33.8 | 31.8 | 30.5 |

As can be seen from the XOX (%) values in Tables 1 and 2 above, the low-temperature clay treatment step (Example 1) of the present invention led to more suppression of decrease in activity of the lipase, and in turn, more improvement in stability of the lipase, in the case where each of the clays were used than in the case where ordinary fat and oil refinement (decolorization•deodorization) was conducted again.

Example 2

Mixture oils each obtained by mixing the refined high-oleic sunflower oil and the ethyl stearate used in Comparative Example 1 at a ratio (mass ratio) of 4:6 were heated to temperatures of 30° C., 50° C., and 80° C., respectively, and were filtered through low-temperature clay treatment vessels (beds) 5 described above at their corresponding temperatures under pressure (a pressure of 0.1 MPa was applied using nitrogen). Then, the mass fraction of water in each oil was adjusted to 200 ppm. Thus, reaction substrates 12 to 14 were obtained. Note that each of the mixture oils of the refined high-oleic sunflower oil and the ethyl stearate was brought into contact with the clay for approximately 1 minute. The temperatures of the reaction substrates 12 to 14 and reaction vessels A prepared as described above were adjusted to 50° C., and each of the reaction substrates 12 to 14 was fed to one of the reaction vessels A (columns) at a rate of 0.2 ml/minute for 64 hours. Thus, transesterified fats and oils 12 to 14 were each obtained. The XOX (%) of each of the transesterified fats and oils 12 to 14 obtained through an outlet of the reaction vessel 64 hours after the start of the reaction was analyzed.

Example 3

Mixture oils each obtained by mixing the refined high-oleic sunflower oil and the ethyl stearate used in Example 1 at a ratio (mass ratio) of 4:6 and low-temperature clay treatment vessels 2 were heated to temperatures of 30° C., 50° C., and 80° C., respectively, and each of the mixture oils was fed to one of the low-temperature clay treatment vessels 2 at a rate of 0.2 ml/minute. Then, the mass fraction of water in each oil was adjusted to 200 ppm. Thus, reaction substrates 15 to 17 were each obtained. The temperatures of reaction vessels A prepared as described above and the reaction substrates 15 to 17 were adjusted to 50° C., and each of the reaction substrates 15 to 17 was fed to one of the reaction vessels A (columns) at a rate of 0.2 ml/minute for 64 hours. Thus, transesterified fats and oils 15 to 17 were each obtained. The XOX (%) of each of the transesterified fats and oils 15 to 17 obtained through an outlet of the reaction vessel 64 hours after the start of the reaction was analyzed.

TABLE 3

|  | Comp. Ex. 1 | Example 2 | | |
| --- | --- | --- | --- | --- |
| Clay treatment vessel | — | 5 | | |
| Reaction vessel | A | A | | |
| Clay treatment temperature | — | 30° C. | 50° C. | 80° C. |
| Reaction substrate | 1 | 12 | 13 | 14 |
| Transesterified fat and oil | 1 | 12 | 13 | 14 |
| XOX(%) | 25.2 | 28.3 | 30.1 | 29.0 |

TABLE 4

|  | Example 3 | | |
| --- | --- | --- | --- |
| Clay treatment vessel | 2 | | |
| Reaction vessel | A | | |
| Clay treatment temperature | 30° C. | 50° C. | 80° C. |
| Reaction substrate | 15 | 16 | 17 |
| Transesterified fat and oil | 15 | 16 | 17 |
| XOX(%) | 30.7 | 33.8 | 33.4 |

In each of the batch-type low-temperature clay treatment step (Example 2) and the continuous low-temperature clay treatment step (Example 3), in which the clay and the fat and oil were brought into contact with each other at temperatures of 30° C. to 80° C., the stability of the lipase was improved in comparison with the case (Comparative Example 1) where no treatment was conducted and the case (Comparative Example 2) where the ordinary decolorization treatment was conducted. Particularly when the treatments were conducted at 50° C. to 80° C., extremely excellent effects on the improvement of the activity of the lipase and the like were obtained. In addition, a comparison of the batch-type treatment (Example 2) with the continuous treatment (Example 3) showed that the continuous treatment achieved better effects on the improvement of the activity of the lipase and the like.

Comparative Example 4

The temperatures of the reaction substrate 1 used in Comparative Example 1 and a reaction vessel B were adjusted to 50° C., and the reaction substrate 1 was fed to the reaction vessel B at a rate of 0.15 ml/minute for 86 hours. Thus, a transesterified fat and oil 18 was obtained. The SOO (%) of each of the transesterified fat and oil obtained through an outlet of the reaction vessel 2 hours and 86 hours after the start of the reaction was analyzed.

Example 4

The temperatures of the reaction substrate 9 used in Example 1 and the reaction vessel B were adjusted to 50° C., and the reaction substrate 9 was fed to the reaction vessel B at a rate of 0.15 ml/minute for 86 hours. Thus, a transesterified fat and oil 19 was obtained. The SOO (%) of the transesterified fat and oil 19 obtained through an outlet of the reaction vessel 2 hours and 86 hours after the start of the reaction was analyzed.

TABLE 5

|  | Comp. Ex. 4 | Example 4 |
| --- | --- | --- |
| Clay treatment vessel | — | 2 |
| Reaction vessel | B | B |
| Clay treatment temperature | 50° C. | 50° C. |
| Reaction substrate | 1 | 9 |
| Transesterified fat and oil | 18 | 19 |
| SOO(%), 2 hours | 27.1 | 28.2 |
| SOO(%), 86 hours | 6.1 | 10.5 |

The stability of the lipase was improved in Example 4 where the low-temperature clay treatment step was conducted in comparison with the case (Comparative Example 4) where no treatment was conducted.

Comparative Example 5

A refined corn oil was obtained by subjecting crude corn oil to decolorization (110° C., 20 minutes, 1% by mass of an activated clay (product name: GALLEON EARTH V2, manufactured by Mizusawa Industrial Chemicals, Ltd.)) and deodorization (260° C., 90 minutes, 400 Pa). The refined corn oil was mixed with medium-chain fatty acid triglyceride (product name: O.D.O, manufactured by The Nisshin OilliO Group, Ltd.) at a mass ratio of 86.5:13.5. Then, the mass fraction of water in the oil was adjusted to 200 ppm. Thus, a reaction substrate 20 was obtained. The temperatures of a reaction vessel A prepared as described above and the reaction substrate 20 were adjusted to 50° C., and the reaction substrate was fed to the reaction vessel A (column) at a rate of 0.2 ml/minute for 64 hours. Thus, a transesterified fat and oil 20 was obtained. The C44(%) of the transesterified fat and oil 20 obtained through an outlet of the reaction vessel 64 hours after the start of the reaction was analyzed.

Example 5

A mixture oil obtained by mixing the refined corn oil and the medium-chain fatty acid triglyceride used in Comparative Example 5 at a mass ratio of 86.5:13.5 was heated to 50° C., and fed to the low-temperature clay treatment vessel 2 (50° C.) at a rate of 0.2 ml/minute. Thus, a low-temperature clay-treated mixture oil was obtained. The raw material (fat and oil) and the clay were brought into contact with each other for 10 minutes. The mass fraction of water in the obtained low-temperature clay-treated mixture oil was adjusted to 200 ppm. Thus, a reaction substrate 21 was obtained. The temperatures of a reaction vessel A (column) prepared as described above and the reaction substrate 21 were adjusted to 50° C., and the reaction substrate 21 was fed to the reaction vessel A at a rate of 0.2 ml/minute for 64 hours. Thus, a transesterified fat and oil 21 was obtained. The C44(%) of the transesterified fat and oil 21 obtained through an outlet of the reaction vessel 2 hours and 64 hours after the start of the reaction was analyzed.

TABLE 6

|  | Comp. Ex. 5 | Example 5 |
|---|---|---|
| Clay treatment vessel | — | Low-temperature clay treatment vessel 2 |
| Reaction vessel | A | A |
| Clay treatment temperature | — | 50° C. |
| Reaction substrate | 20 | 21 |
| Transesterified fat and oil | 20 | 21 |
| C44(%), 2 hours | 14.4 | 18.5 |
| C44(%), 86 hours | 2.8 | 16.0 |

The stability of the lipase was improved in the Example 5 where the low-temperature clay treatment step was conducted in comparison with the case (Comparative Example 5) where no treatment was conducted.

The invention claimed is:

1. A method for producing a transesterified fat and/or oil, comprising:
   (1) a low-temperature clay treatment step of bringing a fat and/or oil and a clay into contact with each other at 30 to 80° C. in the absence of a solvent other than water and in the presence of 200 to 400 ppm of water relative to the total mass of fat and/or oil to obtain a reaction substrate; and
   (2) a step of subjecting the reaction substrate to a transesterification reaction in the presence of a lipase-containing composition.

2. The method according to claim 1, wherein the fat and/or oil used in the low-temperature clay treatment step is a fat and/or oil subjected to a decolorization treatment step of performing decolorization by contact with a first clay at 90 to 150° C.

3. The method according to claim 1, wherein in the low-temperature clay treatment step, the reaction substrate is separated from the clay after the contact with the clay.

4. The method according to claim 2, wherein the fat and/or oil subjected to the decolorization treatment step is subjected to a deodorization step after the decolorization treatment step.

5. The method according to claim 1, wherein the lipase-containing composition is in the form of a powder.

6. The method according to claim 1, wherein the low-temperature clay treatment step is a step of bringing a fat and/or oil, a clay, and a fatty acid ester into contact with one another at 30 to 80° C. to obtain a reaction substrate.

7. The method according to claim 1, wherein the low-temperature clay treatment step of bringing a fat and/or oil and a clay into contact with each other is conducted at 30 to 50° C. in the absence of a solvent other than water to obtain a reaction substrate.

* * * * *